US00PP08513P

United States Patent [19]

Drewlow

[11] Patent Number: Plant 8,513

[45] Date of Patent: Dec. 21, 1993

[54] IMPATIENS PLANT NAMES SERENADE

[75] Inventor: Lyndon W. Drewlow, Ashtabula, Ohio

[73] Assignee: Mikkelsens, Inc., Ashtabula, Ohio

[21] Appl. No.: 858,089

[22] Filed: Mar. 26, 1992

[51] Int. Cl.[5] ..... A01H 5/00
[52] U.S. Cl. ..... Plt./87.6
[58] Field of Search ..... Plt./87.6

*Primary Examiner*—James R. Feyrer
*Assistant Examiner*—E. F. McElwain
*Attorney, Agent, or Firm*—Foley & Lardner

[57] ABSTRACT

A distinct cultivar of impatiens plant named Serenade, characterized by its light lavender flower color, large flower diameter, solid deep green leaves, early flowering, long lasting flowers, excellent self-branching, and its floriferous habit.

1 Drawing Sheet

The present invention relates to a new and distinctive cultivar of Impatiens plant, botanically known as Impatiens, commercially known as New Guinea Impatiens, and known by the cultivar name Serenade. Serenade was developed by me through controlled breeding by crossing Mikkelsen Seedling No. 89-198-1 (seed parent) with Mikkelsen Seedling No. 89-187-3 (pollen parent). Both parents are proprietary breeding lines which have not been sold or made publicly available in this country.

Asexual reproduction carried out by the inventor in Ashtabula, Ohio by terminal or stem cuttings has shown that the unique features of this new impatiens are stabilized and are reproduced true to type in successive propagations.

The following combination of characteristics distinguish the new impatiens from both its parent varieties and other cultivated impatiens of this type known and used in the floriculture industry. Comparisons are made to the cultivar Constellation, Comet and Corona, with the latter two being disclosed in U.S. Plant Pat. Nos. 5,920 and 5,184, respectively. Constellation is not patented.

1. Serenade has a light lavender (81C) flower color similar to Constellation, with Comet and Corona being lavender-purple in flower color (78B and 72B, respectively).

2. Flower diameter of Serenade is larger at 6.0 to 6.5 cm than Constellation at 5.0 cm, Corona at 5.0 to 5.5 cm, and Comet at 5.5 to 6.0 cm.

3. Constellation at 30 to 35 cm and Corona at 25 to 30 cm are taller and more upright than Serenade, a semi-upright cultivar 20 to 25 cm in height. Comet is more mounded and shorter at 15 to 20 cm.

4. Serenade and Corona have solid bright deep green leaves with cream variegation around the midrib of the leaf.

5. The leaves of Serenade and Constellation are similar in size at 11 to 12 cm long and 3.5 to 4.0 cm wide, but larger than Corona (8 to 9 cm long and 3.5 to 4.0 cm wide) and Comet (10 to 11 cm long and 3.0 to 3.5 cm wide).

6. Serenade is 7 to 10 days earlier to flower than Constellation and Corona, and 4 to 7 days earlier than Comet.

7. Both Serenade and Constellation have green midribs and major veins while Comet and Corona have reddish colored midribs and major veins. In addition, Comet has a reddish cast to the entire underside of the leaf.

8. Constellation has the least amount of reddish stem coloration, with the first 1 to 2 cm above the nodes showing color. Serenade has most of its reddish stem coloration in the older main stem tissue, while Comet has most of its coloration in the young apical stem tissue. The entire stem area of Corona is reddish.

9. Serenade and Constellation have light green flower petioles and flower spurs, with the tips of the flower spurs being green. Comet and Corona have reddish purple petioles and spurs with deeper reddish purple tips.

10. Self-branching, early flowering, and its long lasting flowers allows Serenade to be grown in 10 cm pots, but its vigorous habit is such that it can also be grown in 15 to 25 cm containers.

The accompanying color photograph is a front perspective view illustrating the overall appearance of Serenade with the colors being as nearly true as is reasonably possible to obtain in a colored reproduction of this type. The photograph was taken on Apr. 15, 1991, under natural light on an overcast day, under double poly greenhouse covering at Ashtabula, Ohio.

The following is a detailed description of my new cultivar, based on plants produced in greenhouses in Ashtabula, Ohio during the Fall and early Winter season of the year. Plants were grown in 10 cm pots and measurements were taken 12 weeks after rooted cuttings were planted. Height measurements were taken from the soil line of the container. The plants were grown at 65°-68° F. night temperatures, under 3000 to 4000 foot candles of light, and with nutritional values of 250 ppm nitrogen, 75 ppm potassium, and 250 ppm phosphorous, with trace elements added. Heat of growth, foliage coloration, leaf variegation, size of leaves and flower size will be influenced by nutritional and environmental conditions, without, however, any variation in the phenotype.

Color references are made to The Royal Horticultural Society Colour Chart except where general Terms of ordinary dictionary significance are used.

Parentage:

A controlled cross between female parent Mikkelsen Seedling No. 89-198-1 and male parent Mikkelsen Seedling No. 89-187-3.

Propagation:

A. *Type cutting.*—Stem tip 15 mm long will develop to 4 to 5 cm long in 18 to 21 days.

*Time to root.*—8–10 days at 23° C. summer; 10–12 days at 20° C. winter.

C. *Rooting habit.*—Heavy, fibrous.

Plant Description:

A. *Form and habit of growth.*—Semi-upright; self-branched; intermediate in height; vigorous growing; continuous flowering herb; flowering over top of leaf canopy.

B. *Foliage description.*—Bright dark green leaves without variegation. 1. Size: 11 to 12 cm long and 3.5 to 4.0 cm wide. 2. Shape: Lanceolate with acuminate apex and acute base. 3. Texture: Both upper and lower surfaces are glabrous. 4. Margin: Slightly serrated with fine ciliate. 5. Color: young foliage, top side 137A. under size 146B. mature foliage, top side 147A. under side 147B. 6. Venation: Pinnate, green in color.

Flowering description:

A. *Flowering habits.*—Flowers continuously from leaf whorl in a progressive orderly manner, with one flower per leaf axil the normal number. When last flower in a leaf whorl opens the first flower in the leaf whorl above starts to open. It takes 5 to 7 days for a mature bud to fully open and then the flower may last 2 weeks or longer depending on the environment.

B. *Natural flowering season.*—Indeterminant and continuous. Quantity of flowering increases with increasing levels of light.

C. *Flower buds.*—Ellipsoidal, flowers perfect. Light green spur up to 6.0 cm long with green tip on a mature bud, with throat behind the ovary and originating from the major sepal.

*Flowers borne.*—On individual 4.0 cm long green pedicels from a whorl of usually 5 leaves, flowering progressively around the whorl as buds and leaves develop. Most leaf axils have one flower.

E. *Quantity of flowers.*—Numerous because of long lasting flowers and highly self-branched nature of plant. Flower development is continuous and is above leaf canopy.

F. *Diameter of flower.*—6.0 to 6.5 cm.

G. *Petals*—1. Shape: Heart; two keel petals are largest. 2. Color: Top side in winter when opening, 81C, fading to 82C to 82D; underside 76B to 76C. the petals form near their bases a white central eye, 155° C. 3. Number of petals: 5. 4. Size of petals: Standard: 4.0 cm wide and 2.5 cm long; two equal lobes shallow cut. Wings: 2.5 cm wide and 2.5 cm long; two unequal lobes, intermediate cut. Keel: 3.5 cm wide and 3.5 cm long; two unequal lobes deep cut.

H. *Reproductive organs.*—1. Stamens: Five (5) in number. a. Anther shape: Hooded, color white. b. Pollen color: White. 2. Pistils: a. Stigma shape: 5 Segmented column, color white. b. Style color: White. c. Ovaries: Five (5) in number, size 4 mm when receptive, color green.

Disease resistance: No significant disease or insect problems seen to date.

OTHER IMPORTANT CHARACTERISTICS

1. Flowers of Serenade are longer lasting than Comet and Constellation and similar to Corona.
2. Serenade has demonstrated the ability to tolerate both high temperature and sunlight levels as well as cool temperatures (40°–50° F.). Thus, the growing season can be extended.

I claim:

1. A new and distinct impatiens plant named Serenade, as illustrated and described.

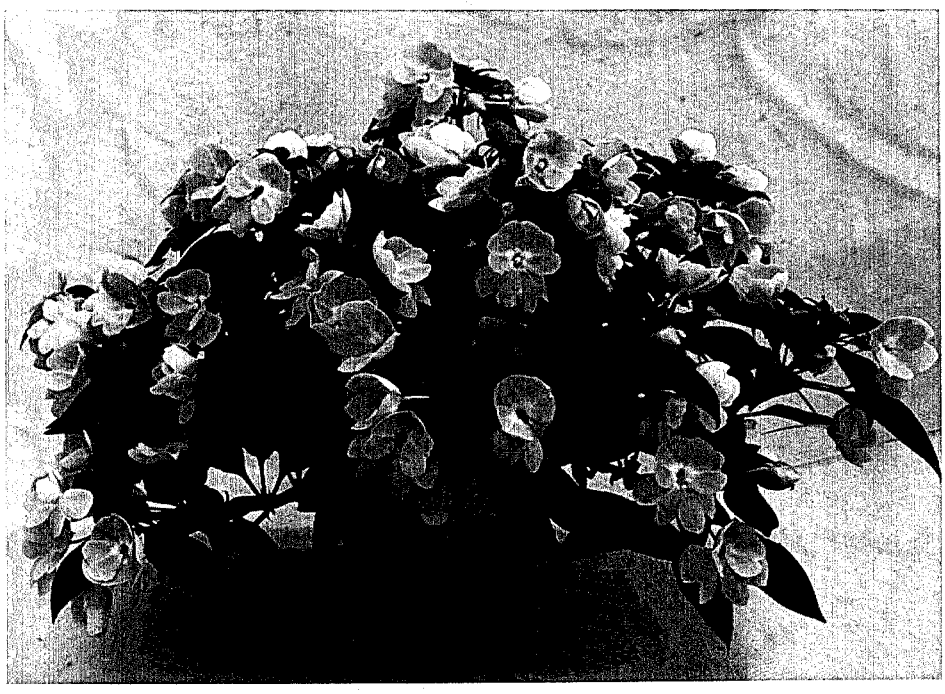

* * * * *